US012653766B2

(12) United States Patent
Cal et al.

(10) Patent No.: US 12,653,766 B2
(45) Date of Patent: Jun. 16, 2026

(54) COMPOSITION COMPRISING A COMBINATION CONSISTING OF MAGNOLOL AND HONOKIOL, USE OF THE COMPOSITION, METHOD OF MANUFACTURING THE COMPOSITION, AND COSMETIC PRODUCTS COMPRISING THE COMPOSITION AND METHOD OF MANUFACTURING THEREOF

(71) Applicants: LABORATORIUM INŻYNIERII CZĄSTEK KRZYSZTOF CAL, Gdansk (PL); Irena Eris Spółka Akcyjna, Piaseczno (PL)

(72) Inventors: Krzysztof Cal, Gdansk (PL); Irena Szołomicka-Orfinger, Warsaw (PL); Katarzyna Rogiewicz, Milanowek (PL); Renata Dębowska, Mńsk Mazowiecki (PL); Anna Kuranc, Warsaw (PL); Monika Pasikowska-Piwko, Warsaw (PL); Monika Gębczyńska-Rzepka, Piaseczno (PL)

(73) Assignees: Irena Spolka Akcyjna, Piaseczno (PL); LABORATORIUM INZYNIERII CZASTEK KRZYSZTOF CAL, Gdansk (PL)

( * ) Notice: Subject to any disclaimer, the term of this patent is extended or adjusted under 35 U.S.C. 154(b) by 133 days.

(21) Appl. No.: 18/240,438

(22) Filed: Aug. 31, 2023

(65) Prior Publication Data

US 2024/0082124 A1 Mar. 14, 2024

(30) Foreign Application Priority Data

Aug. 31, 2022 (PL) ...................................... P.442160

(51) Int. Cl.

*A61K 8/34* (2006.01)
*A61Q 19/00* (2006.01)

(52) U.S. Cl.

CPC ............ *A61K 8/347* (2013.01); *A61Q 19/007* (2013.01); *A61K 2800/5922* (2013.01); *A61K 2800/805* (2013.01)

(58) Field of Classification Search

None

See application file for complete search history.

(56) References Cited

U.S. PATENT DOCUMENTS

| | | | | |
|---|---|---|---|---|
| 2017/0281481 | A1* | 10/2017 | Pacchetti | A61K 8/042 |
| 2021/0267857 | A1 | 9/2021 | Faller | |

FOREIGN PATENT DOCUMENTS

| | | | |
|---|---|---|---|
| CN | 114712259 | A | 7/2022 |
| CN | 113440426 | A | 3/2023 |
| EP | 2455134 | A2 | 5/2012 |
| PL | 223601 | A2 | 5/1981 |
| PL | 440431 | | 2/2022 |
| WO | 2008130752 | A2 | 10/2008 |
| WO | 2013149323 | A1 | 10/2013 |
| WO | 2016073529 | A1 | 5/2016 |

OTHER PUBLICATIONS

Jui-Lung Shen, “Honokiol and magnolol as multifunctional antioxidative molecules for dermatologic disorders”, Molecules 2010, DOI: 10.3390/molecules 15096452.

Dr. Irene Montano, Magnolia Derived Honokiol and Magnolol Fight Against Skin Inflamm“Aging”, Mibelle Biochemistry 2010.

Iris Usach, “Magnolol and Honokiol: Two Natural Compounds with Similar Chemical Structure but Different Physicochemical and Stability Properties”, Pharmaceutics 2021, DOI: 10.3390/pharmaceutics13020224.

* cited by examiner

*Primary Examiner* — Nicole P Babson

(74) *Attorney, Agent, or Firm* — Dickinson Wright PLLC; Andrew D. Dorisio; Ina Agaj

(57) ABSTRACT

A cosmetic composition comprising a combination includes magnolol and honokiol or their cosmetically acceptable derivatives, along with the use of such a composition, a method of manufacturing thereof, as well as cosmetic products including such a composition and methods of manufacturing thereof.

18 Claims, 3 Drawing Sheets

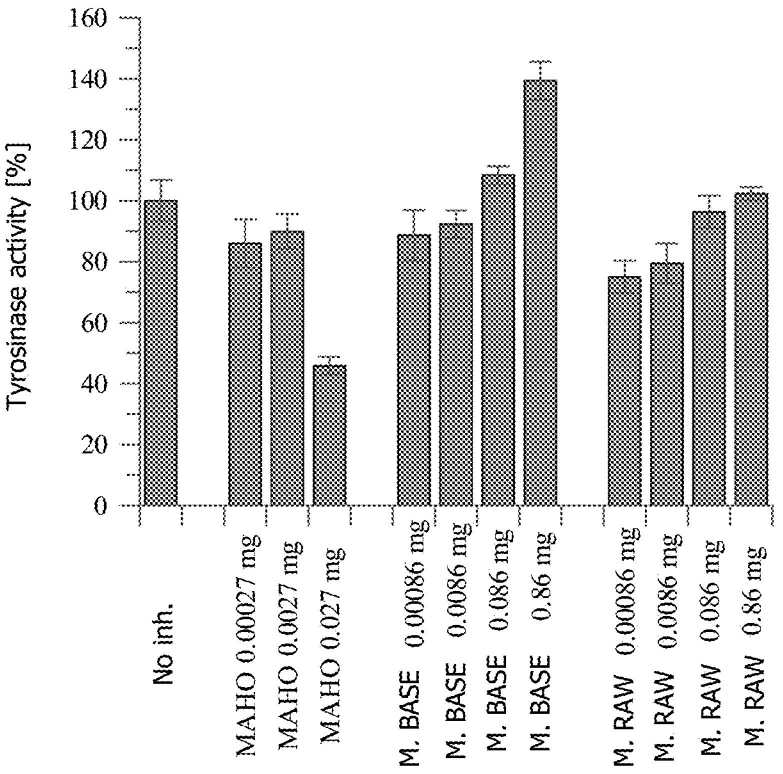
*Fig. 1 Tyrosinase inhibitory activity (measurement 1)*
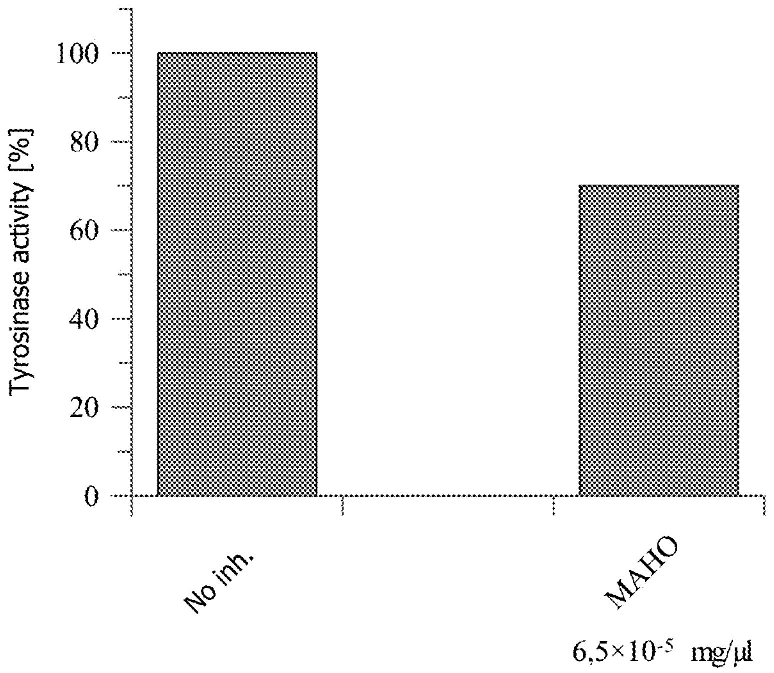
*Fig. 2 Inhibitory activity assay conducted in polystyrene cuvettes using a spectrophotometer (measurement 2)*

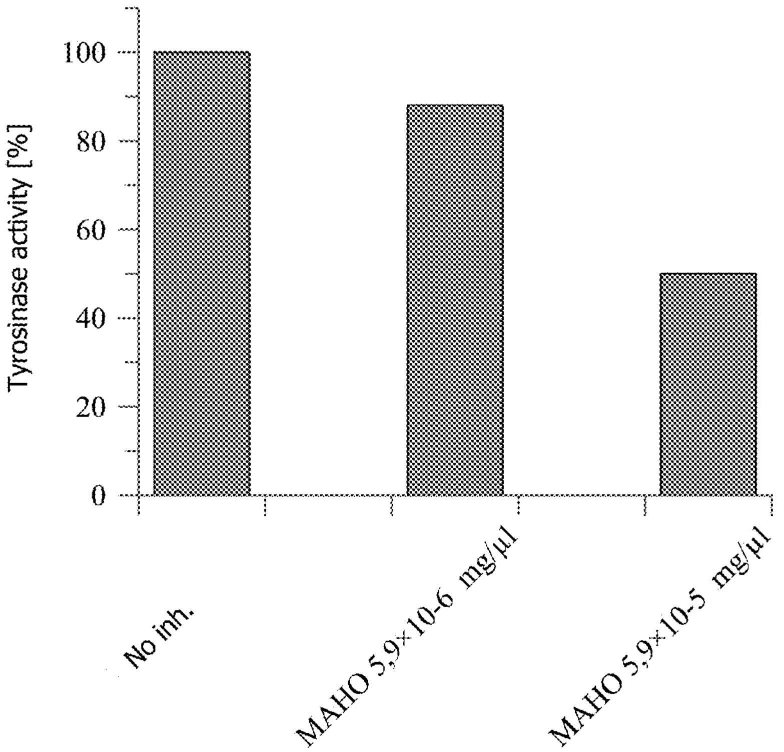
*Fig. 3 Inhibitory activity assay conducted in polystyrene cuvettes using a spectrophotometer (measurement 3)*
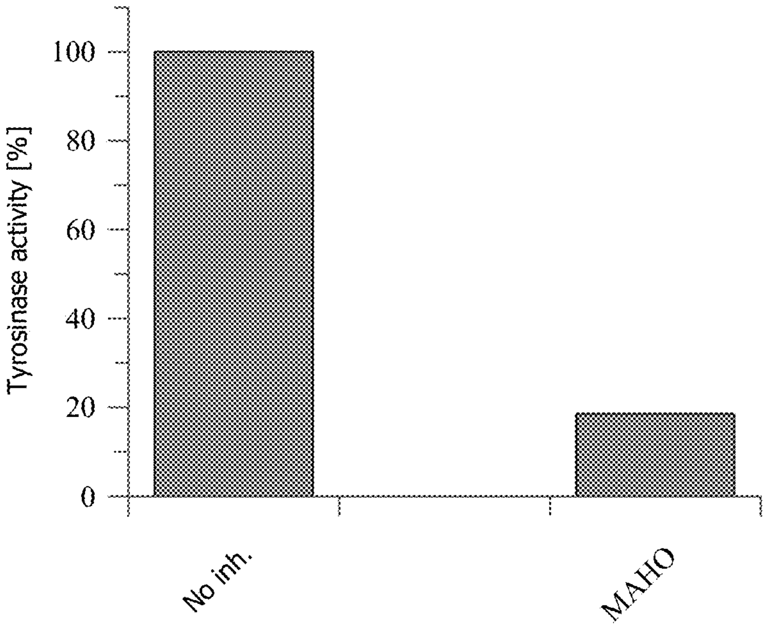
*Fig. 4 Inhibitory activity assay conducted in polystyrene cuvettes using a spectrophotometer (measurement 4)*

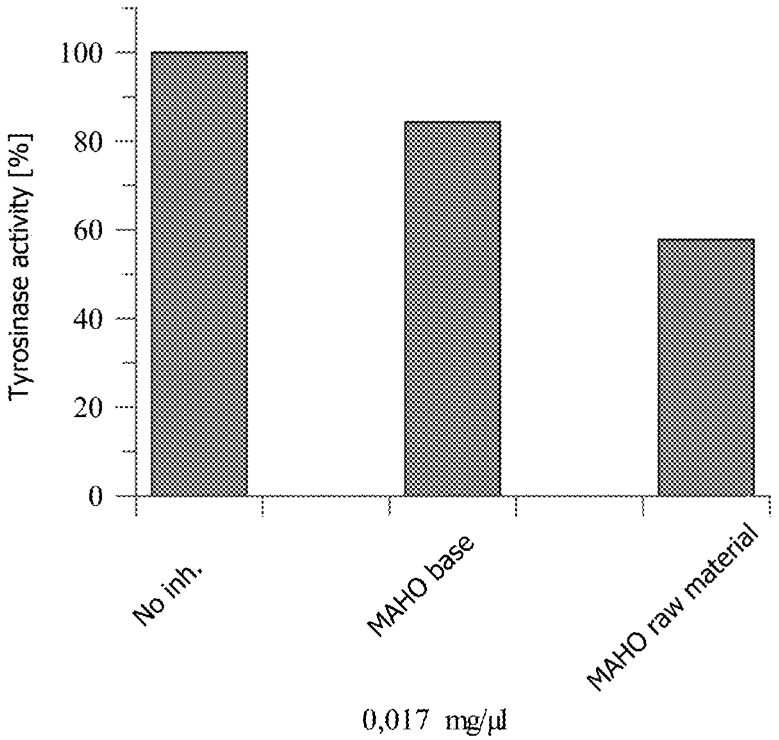
*Fig. 5 Inhibitory activity assay conducted in polystyrene cuvettes using a spectrophotometer (measurement 5)*

COMPOSITION COMPRISING A COMBINATION CONSISTING OF MAGNOLOL AND HONOKIOL, USE OF THE COMPOSITION, METHOD OF MANUFACTURING THE COMPOSITION, AND COSMETIC PRODUCTS COMPRISING THE COMPOSITION AND METHOD OF MANUFACTURING THEREOF

This application claims priority to Polish Application No. P.442160 filed on Aug. 31, 2022, the disclosure of which is incorporated herein by reference.

FIELD OF INVENTION

The invention relates to a cosmetic composition comprising a combination of magnolol and honokiol or their cosmetically acceptable derivatives. The invention also relates to the use of such a composition, a method of manufacturing thereof, as well as cosmetic products comprising such a composition and methods of manufacturing thereof.

STATE OF THE ART

Magnolol and honokiol are small-molecule polyphenols isolated from plants of the *magnolia* genus. They exhibit a potent antioxidant, anti-inflammatory, antitumour and antimicrobial activity, and thus there is high interest in using these active compounds in dermatological and cosmetic agents.

EP2455134 reveals a composition for the treatment of skin conditions such as eye circles or puffy eyes, comprising *magnolia* extract. The active ingredients of the composition of EP2455134 are magnolol and honokiol, which, according to the description of the invention, have the effect of reducing blood flow at the skin surface. These compounds are included in the extract of the *Magnolia* genus plant. In addition to active ingredients, the document mentions a number of auxiliary substances such as moisturizers, emollients, surfactants, preservatives, antioxidants or thickening agents, among others.

CN113440426A relates to a method of obtaining a honokiol product having a good solubility, high stability and high biocompatibility. The method involves encapsulating honokiol with a starting composition comprising 1-5% of magnolol, 1-10% of lecithin, 1-15% of liquid oil, 1-15% of emulsifier, 0.1-5% of lignin or its derivatives, and water up to 100%. The composition thus prepared comprises 1-5% of honokiol micelles of 20-30 nm in size.

From international application WO2016073529A1, an anti-aging composition is known, which reduces visible signs of skin aging. The composition according to WO2016073529A1 comprises at least one neolignan, ectoin, and an organic compound of formula (I). In a preferred embodiment of WO2016073529A1, the neolignan in the composition is honokiol. In a particularly preferred embodiment, the composition may comprise *magnolia* bark extract on a lecithin carrier, which allows the *magnolia* bark extract to dissolve in fats.

WO2013149323A1 discloses an excipient and a cosmetic composition for application to the skin, comprising water and at least one vegetable oil extract and at least one lipophilic additive dissolved in said oil. The contents of WO2013149323A1 disclose a number of groups of several composition ingredients, both cosmetically active, as well as auxiliary. Ingredients according to WO2013149323A1 may include (as ingredients of these groups) magnolol, honokiol, glycerol, soy lecithin, sodium benzoate, potassium sorbate and glycerol, among others, however none of the examples describe a specific composition comprising magnolol and/or honokiol.

Publication by Jui-Lung Sheni et al, "Honokiol and Magnolol as Multifunctional Antioxidative Molecules for Dermatologic Disorders," Molecules, 15, 6452-6465 (publication date: Sep. 16, 2010) reviewed publications on the properties of magnolol and honokiol, and in particular on overall antioxidant activity, anti-inflammatory and anticancer properties, and antimicrobial properties.

Publication by Dr. Irene Montano and Dr. Daniel Schmid., "*Magnolia* Derived Honokiol and Magnolol Fight Against Skin Inflamm'Aging," Mibelle Biochemistry, Switzerland, February 2010, describes how to produce a cosmetic ingredient based on *Magnolia* bark extract that is free of preservatives and alcohol and exhibits good absorption. The publication reports that the cosmetic ingredient comprises an aqueous-ethanol extract of *magnolia* bark, which, combined with maltodextrin and a carrier, makes it possible to obtain liposomes with lecithin. The publication, however, is silent on the amounts of substrates (especially lecithin) used for manufacture.

Publication by Iris Usach, José-Esteban Peris et al. "Magnolol and Honokiol: Two Natural Compounds with Similar Chemical Structure but Different Physicochemical and Stability Properties," Pharmaceutis, 2021, 13, 224 presents the results of physicochemical studies of magnolol and honokiol. One of the aspects revealed in the publication is a method of preparing liposomes comprising honokiol. According to the disclosure, the liposomes were obtained from: phosphatidylcholine, honokiol, ethanol and twice-distilled water. The dispersion obtained from the previously mentioned ingredients was subjected to ultrasonic homogenization. The resulting liposomes do not comprise lecithin.

It would therefore be desirable to develop cosmetic compositions comprising magnolol and honokiol, which would show high stability and would be suitable for use in topical preparations, for example skin preparations, without occurrence of any adverse effects, providing an effective cosmetic effect with cosmetically active agents in low concentrations, and which, at the same time, would be easy to produce without involving extraordinary technical means.

SUMMARY OF THE INVENTION

The subject of the invention is a cosmetic composition comprising:

| | |
|---|---|
| 0.5 to 20.00% by weight | of solvent - glycerol |
| 0.3 to 13.00% by weight | of thickening agent selected from the group consisting of cellulose, hydroxyethylcellulose and their mixtures, |
| 0.5 to 5.00% by weight | of emulsifier - lecithin, |
| 0.5 to 10.00% by weight | of preservative booster/emollient - ethylhexylglycerin, |
| 0.1 to 10.00% by weight | of magnolol or its cosmetically acceptable derivative, |
| 0.1 to 10.00% by weight | of honokiol or its cosmetically acceptable derivative, |
| 0.5 to 1.00% by weight | of at least one preservative selected from the group comprising potassium sorbate, sodium benzoate and their mixtures, |
| and up to 100% by weight | of water, |

wherein the percentages are expressed based on total weight of the composition.

Preferably, the composition according to the invention comprises

| | |
|---|---|
| 10.0% by weight | of glycerol, |
| 3.0% by weight | ofcellulose, |
| 1.0% by weight | of lecithin, |
| 1.0% by weight | of ethylhexylglycerin, |
| 1.0% by weight | of hydroxyethylcellulose, |
| 1.0% by weight | of magnolol, |
| 1.0% by weight | of honokiol, |
| 0.5% by weight | of potassium sorbate, |
| 0.5% by weight | of sodium benzoate, |
| 81.0% by weight | of water, |

wherein the percentages are expressed based on the total weight of the composition.

Preferably, magnolol and honokiol are present in the composition of the invention in the form of an extract having a concentration of about 90 to about 98% by weight.

In another embodiment, magnolol and honokiol are present in the composition of the invention in an isolated form.

The subject of the invention is also a method of manufacturing the cosmetic composition of the invention comprising the following steps:

a) preparing a mixture of composition ingredients except lecithin and hydroxyethylcellulose, b) dissolving and hydrating lecithin in the resulting mixture, c) homogenizing the resulting mixture, and d) adding hydroxyethylcellulose and mixing the resulting composition.

Preferably, the step of dissolving and hydrating lecithin is carried out for at least 24 hours.

The subject of the invention is also a cosmetic product comprising the cosmetic composition according to the invention.

Preferably, the cosmetic product comprises 0.5-1.5%, preferably 1.0% by weight of the composition as defined herein based on the total weight of the cosmetic product.

Preferably, the cosmetic product is selected from a group comprising emulsions, in particular, such as cream, lotion, milk and facial serum.

Preferably, the cosmetic product comprises

| | |
|---|---|
| 0.10-10.00% by weight | of at least one humectant, |
| 0.20-3.00% by weight | of at least one preservative, |
| 0.10-5.00% by weight | of at least one thickening agent, |
| 2.50-10.00% by weight | of at least one emulsifier, |
| 10.00-35.00% by weight | of at least one emollient, |
| 0.10-1.50% by weight | of the composition as defined in any of claims 1-3, |
| 0.10-10.00% by weight | of additional cosmetically active substances, |
| 0.05-1.00% by weight | of at least one additive, |
| and up to 100% by weight | of water, |

based on the total weight of the cosmetic product.

Preferably, the cosmetic product additionally comprises 0.20-0.50% by weight of a fragrance composition.

Preferably, the cosmetic product comprises 10.00 to 15.00% by weight of at least one UV filter.

Preferably, the cosmetic product is selected from a group comprising emulsions, particularly in the form of a cream, including day cream, night cream, under-eye and eyelid cream, and natural cream, lotion, milk and facial serum.

In a preferred embodiment, the cosmetic product is in the form of a day and night cream, and comprises:

| | |
|---|---|
| 2.00-4.00% by weight | of at least one humectant, |
| 0.20-0.60% by weight | of at least one preservative, |
| 0.10-0.50% by weight | at least one thickening agent, |
| 2.50-4.50% by weight | of at least one emulsifier, |
| 10.00-15.00% by weight | of at least one emollient, |
| 0.50-1.50% by weight | of the composition, |
| 1.00-3.00% by weight, | of at least one additional cosmetically active substance, |
| 0.30-0.50% by weight | of fragrance composition, |
| 0.20-0.60% by weight | of at least one additive, |
| and up to 100% by weight | of water |

based on the total weight of the cosmetic product

In a preferred embodiment, the cosmetic product is in the form of a night cream, and comprises:

| | |
|---|---|
| 0.10-1.00% by weight | of at least one humectant, |
| 0.50-1.00% by weight | of at least one preservative, |
| 0.10-0.20% by weight | of at least one thickening agent, |
| 5.00-10.00% by weight | of at least one emulsifier, |
| 30.00-35.00% by weight | of at least one emollient, |
| 0.50-1.50% by weight | of the composition, |
| 2.00-3.00% by weight, | of at least one additional cosmetically active substance, |
| 0.20-0.40% by weight | of fragrance composition, |
| 0.05-1.00% by weight | of at least one additive, |
| and up to 100% by weight | of water |

based on the total weight of the cosmetic product.

In a preferred embodiment, the cosmetic product is in the form of a day cream, and comprises:

| | |
|---|---|
| 3.00-5.00% by weight | of at least one humectant, |
| 1.00-1.50% by weight | of at least one preservative, |
| 1.50-3.50% by weight | of at least one thickening agent, |
| 3.50-5.50% by weight | of at least one emulsifier, |
| 10.00-15.00% by weight | of at least one UV filter, |
| 15.00-25.00% by weight | of at least one emollient, |
| 0.50-1.50% by weight | of the composition, |
| 1.00-2.00% by weight, | of at least one additional cosmetically active substance, |
| 0.30-0.50% by weight | of fragrance composition, |
| 0.05-0.15% by weight | of at least one additive, |
| and up to 100% by weight | of water |

based on the total weight of the cosmetic product

In a preferred embodiment, the cosmetic product is in the form of an under-eye cream, and comprises:

| | |
|---|---|
| 2.00-4.00% by weight | of at least one humectant, |
| 0.50-1.00% by weight | of at least one preservative, |
| 0.10-1.00% by weight | of at least one thickening agent, |
| 4.50-6.50% by weight | of at least one emulsifier, |
| 10.00-15.00% by weight | of at least one emollient, |
| 0.50-1.50% by weight | of the composition, |
| 5.00-10.00% by weight, | of at least one additional cosmetically active substance, |
| 0.05-0.15% by weight | of at least one additive, |
| and up to 100% by weight | of water |

based on the total weight of the cosmetic product.

In a preferred embodiment, the cosmetic product is in the form of a facial serum, and comprises:

| | |
|---|---|
| 5.00-10.00% by weight | of at least one humectant, |
| 0.50-1.00% by weight | of at least one preservative, |
| 0.50-1.50% by weight | of at least one thickening agent, |
| 3.00-5.00% by weight | of at least one emulsifier, |

-continued

| | |
|---|---|
| 10.00-15.00% by weight | of at least one emollient, |
| 0.50-1.50% by weight | of the composition, |
| 0.10-1.00% by weight | of at least one additional cosmetically active substance, |
| 0.20-0.40% by weight | of fragrance composition, |
| 0.20-0.40% by weight | of at least one additive, |
| and up to 100% by weight | of water |

based on the total weight of the cosmetic product.

In a preferred embodiment, the cosmetic product is in the form of a natural cream, and comprises:

| | |
|---|---|
| 4.00-6.00% by weight | of at least one humectant, |
| 0.60-1.30% by weight | of at least one preservative, |
| 0.10-0.30% by weight | of at least one thickening agent, |
| 3.50-4.50% by weight | of at least one emulsifier, |
| 17.00-24.00% by weight | of at least one emollient, |
| 0.50-1.50% by weight | of the composition, |
| 0.15-0.50% by weight | of at least one additive, |
| and up to 100% by weight | of water |

based on the total weight of the cosmetic product.

Preferably, at least one additive is selected from a group comprising at least one pH adjusting agent, at least one chelating agent and at least one colorant.

The subject of the invention is also a method of manufacturing the cosmetic product of the invention, characterized in that it comprises a) preparing an aqueous phase and heating it to an elevated temperature, b) preparing an oil phase and heating it to an elevated temperature, c) adding an emulsifier to the oil phase and mixing, d) adding the aqueous phase to the oil phase and homogenizing the resulting mixture, e) optionally cooling the resulting mixture and adding a UV filter, f) cooling the resulting mixture, g) adding cosmetically active ingredients, a preservative and optionally a fragrance composition, and then homogenizing the resulting mixture, h) further cooling the resulting mixture.

The combination of magnolol and honokiol in a single cosmetic composition allows for obtaining a technical effect of improving skin firmness and smoothness, as well as reducing hyperpigmentation and redness after 4 weeks of the composition application.

In addition, the method of manufacturing the composition of the invention does not require extraordinary technical means.

Cosmetic products consisting of or comprising the composition of the invention provide slowing down the skin aging processes, equalizing skin tone, brightening skin (hyperpigmentation), improving the overall appearance of the skin, gently smoothing the skin, preventing the formation of new fine lines and wrinkles and reducing the existing ones, and regenerating the skin.

BRIEF DESCRIPTION OF THE DRAWING FIGURES

FIG. 1 shows tyrosinase inhibitory activity—comparison of MAHO, MAHO base (M. BASE), MAHO raw material (M. RAW) (measurement 1)

FIG. 2 shows the assay results of inhibitory activity conducted in polystyrene cuvettes using a spectrophotometer (measurement 2)

FIG. 3 shows the assay results of inhibitory activity conducted in polystyrene cuvettes using a spectrophotometer (measurement 3)

FIG. 4 shows the assay results of inhibitory activity conducted in polystyrene cuvettes using a spectrophotometer (measurement 4)

FIG. 5 shows the assay results of inhibitory activity conducted in polystyrene cuvettes using a spectrophotometer (measurement 5)

DETAILED DESCRIPTION

Definitions

As used in this description, the term "cosmetically acceptable derivative" refers to compounds derived from magnolol and honokiol, such as cosmetically acceptable salts, esters, solvates, hydrates and the like, which exhibit similar activity and can be used as substitutes for magnolol and honokiol.

As used in this description, the term "cosmetically active ingredient" refers to a substance that exhibits a cosmetic or caring effect, preferably on the skin. This term does not include auxiliary ingredients of the composition according to the subject invention and products comprising it, which provide functional characteristics, e.g. stability, consistency, fragrance, etc.

As used in this description, the term "natural cream" means a cream comprising essentially only ingredients of natural origin. Natural cream may, but does not have to, comprise ingredients of synthetic origin which in their structure correspond to analogous ingredients of natural origin.

The cosmetically active ingredient in the composition according to the invention is a combination consisting of magnolol and honokiol, wherein those are the only active ingredients in the composition.

Magnolol (5,5"-diallyl-2,2"-dihydroxybiphenyl) of the following formula:

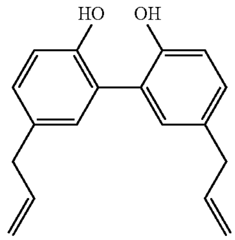

, and honokiol (3",5-diallyl-2,4"-dihydroxybiphenyl) of the formula:

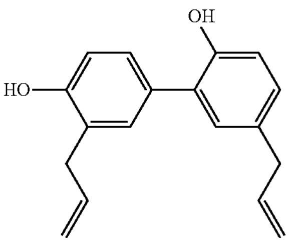 [SMILES: C=CCc1ccc(O)c(-c2ccc(O)c(CC=C)c2)c1]

are neolignans found in the bark of houpu *magnolia* (*Magnolia officinalis*). These compound are tyrosinase inhibitors with no cytotoxicity, characterized by anti-oxidant, antitumour or anti-inflammatory properties, among others.

Magnolol may be present in the composition according to the invention in an amount of about 0.1 to about 10% by weight, and especially in an amount of 1.0% by weight, based on the total weight of the composition.

Honokiol may be present in the composition according to the invention in an amount of about 0.1 to about 10% by weight, and in particular in an amount of 1.0% by weight, based on the total weight of the composition.

Magnolol and honokiol may be present in the composition of the invention in the form of an extract having a concentration of about 90 to about 98% by weight. Alternatively, these compounds may be present in the composition according to the invention in an isolated form, for example, as isolated from said extract. A person skilled in the art will know which extracts can be used in said composition, as well as how said compounds can be isolated.

In addition to said combination of magnolol and honokiol, the composition of the invention, in particularly preferable embodiments, may comprise auxiliary ingredients that provide, among other things, the proper form and stability of the composition of the invention.

Glycerol is used in the composition of the invention as a solvent. Glycerol may be present in the composition according to the invention in an amount of about 0.5 to about 20.00% by weight, and in particular in an amount of about 10.00% by weight, based on the total weight of the composition. Within the scope of the invention, any type of glycerol can be used, but in a preferred embodiment of the invention, glycerol of plant origin is used.

Ethylhexylglycerin may be present in the composition according to the invention in an amount of about 0.1 to about 10.0% by weight, and in particular in an amount of about 1.00% by weight based on the total weight of the composition. This ingredient boost the effect of preservatives and acts as emollient.

The cellulose used in the composition according to the invention acts as a thickening agent and provides texture to the composition. Cellulose may be present in the composition according to the invention in an amount of about 0.5 to about 10.00% by weight, and in particular in an amount of about 3.00% by weight based on the total weight of the composition. Within the scope of the invention, cellulose of any origin can be used, wherein in a preferred embodiment of the invention bamboo cellulose is used.

Lecithin is used in the composition according to the invention as an emulsifier. Lecithin may be present in the composition according to the invention in an amount of about 0.5 to about 5.00% by weight, and in particular in an amount of about 1.00% by weight based on the total weight of the composition. Within the scope of the invention, lecithin of any origin can be used, wherein in a preferred embodiment of the invention sunflower lecithin is used.

The composition may also comprise at least one preservative selected from a group comprising sodium benzoate and potassium sorbate. Preferably, a combination of sodium benzoate and potassium sorbate is used.

At least one preservative may be present in the composition according to the invention in an amount of about 0.5 to about 1.00% by weight based on the total weight of the composition.

When a combination of sodium benzoate and potassium sorbate is used, sodium benzoate may be present in the composition according to the invention in an amount of from about 0.4 to about 0.6% by weight, and in particular in an amount of about 0.50% by weight based on the total weight of the composition, and potassium sorbate may be present in the composition according to the invention in an amount of from about 0.4 to about 0.6% by weight, and in particular in an amount of about 0.50% by weight based on the total weight of the composition.

Hydroxyethylcellulose (HEC) is used in the composition according to the invention as a thickening agent. Hydroxyethylcellulose may be present in the composition according to the invention in an amount of about 0.3 to about 3.00% by weight, and in particular in an amount of about 1.00% by weight based on the total weight of the composition.

The composition according to the invention can be manufactured by any method known in the field of the invention, but preferably it is manufactured by a method comprising the following steps:

preparing a mixture of composition ingredients except lecithin and hydroxyethylcellulose, dissolving and hydrating lecithin in the resulting mixture, homogenizing the resulting mixture, and adding hydroxyethylcellulose and mixing resulting composition.

The step of dissolving and hydrating lecithin is carried out by means of any method known in the art for a period of time typically known to a skilled person, but is preferably carried out for a period of at least 24 hours, more preferably for up to 24 hours, particularly preferably for 24 hours.

Homogenization of the mixture can be carried out by any technique used in the art. For example, without limiting the scope of the invention, high-speed homogenization or high-pressure homogenization can be used. The homogenization step, resulting in fine grinding and perfect mixing of the mixture ingredients, provides, among other things, stability and better consistency of the mixture.

In simple terms, high-speed homogenization involves subjecting a mixture to mechanical forces through intense and rapid mixing. According to the invention, homogenization using this technique can be preferably carried out at a speed of 20000 rpm fora period of 10 minutes.

High-pressure homogenization is one of the most widely used homogenization techniques. In simple terms, it involves pumping the mixture through a specially designed valve with a very small, adjustable clearance.

Addition of hydroxyethylcellulose and mixing of the resulting mixture in the last step of the method leads to the transformation of the composition from a liquid form into a gel form. Gelation process can also be carried out by any other method, as well as with use of other alternative thickening agents, for example, other cellulose derivatives or natural gums.

Among other things, the composition according to the invention can be used for cosmetic and personal care purposes—as an ingredient of cosmetic bases or cosmetic products.

Typically, a cosmetic product is a complete product, ready for use. Cosmetic products comprising the composition according to the invention are usually produced by adding said composition to base of appropriate cosmetic product, possibly with additional active ingredients.

Unlike cosmetic products, a cosmetic base is a base that can only be used to produce products such as cosmetic products, by, for example, combining it with other, additional active ingredients and/or auxiliary ingredients.

The cosmetic product, as well as the cosmetic base, can consist only of the composition according to the subject invention. In a preferred embodiment of the invention, the composition according to the invention can be an ingredient of a cosmetic product or a cosmetic base. Typically, the composition according to the invention constitutes from about 0.50 to about 100% by weight of the total weight of the cosmetic base or product. Less than about 0.50% of the composition does not provide the desired effects.

Preferably, the composition according to the invention is present in the cosmetic product or cosmetic base in an amount of about 0.50 to about 1.50% by weight based on the total weight of the cosmetic product or base. Preferably, the composition according to the invention is present in the cosmetic product or cosmetic base in an amount of about 1.00% by weight based on the total weight of the cosmetic base or product.

The other ingredients of the cosmetic base or product are typical and depend on the type and/or intended use and/or method of use of the cosmetic base or product. The amount of these ingredients also depends on the type and/or intended use of the cosmetic base or product. The type and amount of additional ingredients can be selected by a person skilled in the art.

The composition according to the invention can be used in any cosmetic product, but in a preferred embodiment of the invention the composition is used in products having the form of an emulsion, in particular, such as cream, lotion, milk, facial serum and tonic, and particularly preferably in the forms indicated in Examples.

Said additional ingredients of the cosmetic base or product may include, but are not limited to:

- humectants (moisture-binding agents) (e.g., glycerol or propanediol) and mixtures thereof
- preservatives (such as, but not limited to: hydroxyacetophenone (INCI: Hydroxyacetophenone); Japanese honeysuckle flower extract (INCI: *Lonicera Japonica* Flower Extract), perfoliate honeysuckle flower extract (INCI: *Lonicera* Caprifolium Flower Extract); particularly in a mixture comprising these two extracts, hexylene glycol (INCI: Hexylene Glycol), pentylene glycol (INCI: Pentylene Glycol), 4-(4-hydroxyphenyl)-2-butanone (INCI: Raspberry Ketone), and mixtures thereof).
- thickening agents (such as, but not limited to: xanthan gum (INCI: Xanthan Gum), gum arabic (INCI: Acacia Senegal Gum), carbomer (INCI: Carbomer), carbomer sodium (INCI: Sodium Carbomer), magnesium-aluminum silicate (INCI: Magnesium Aluminum Silicate), hectorite (INCI: Hectorite), hectorite modified with stearalkonium salt (INCI: Stearalkonium hectorite), bentonite (INCI: Bentonite), *sclerotium* gum (INCI: *Sclerotium* Gum), and mixtures thereof).
- emulsifiers (such as, but not limited to: stearoyl glutamate sodium salt (INCI: Sodium Stearoyl Glutamate), a mixture of cetearyl glucoside, cetyl alcohol and stearyl alcohol (INCI: Cetearyl Glucoside, Cetearyl Alcohol), cetyl phosphate potassium salt (INCI: Potassium Cetyl Phosphate), glyceryl stearate (INCI: Glyceryl Stearate), glyceryl stearate citrate (INCI: Glyceryl Stearate Citrate), a mixture of C14-C22 alcohols, C12-C20 alkyl glucosides (INCI: C14-22 Alcohols, C12-20 Alkyl Glucoside), a mixture of arachidyl glucoside, arachidyl alcohol and behenyl alcohol (INCI: Arachidyl Glucoside, Arachidyl Alcohol, Behenyl Alcohol), and mixtures thereof),
- UV filters (substances that reflect or absorb UV radiation, including physical and chemical UV filters, as well as mixtures thereof) (such as, but not limited to: 2-ethylhexyl salicylate (CAS: 118-60-5), 2,2'-[6-(4-methoxyphenyl)-1,3,5-triazine-2,4-diyl]bis{5-((2-ethylhexyl)oxy)-phenol (CAS: 187393-00-6), tris(2-ethylhexyl)-4,4',4"-(1,3,5-triazine-2,4,6-triyltriimino)tribenzoate (CAS: 88122-99-0); diethylamino hydroxybenzoyl hexyl benzoate (CAS: 302776-68-7); a mixture of titanium dioxide, caprylic/capric acid triglycerides, poly(hydroxystearic acid), stearic acid and alumina; 2,2'-methylenebis[6-(2H-1,2,3-benzotriazol-2-yl)-4-(2,4,4-trimethylpentan-2-yl)phenol] (CAS: 103597-45-1), and mixtures thereof).
- emollients selected from fatty alcohols, esters and natural oils (such as, but not limited to: hexanedioic acid 1,6-dibutyl ester (INCI: Dibutyl Adipate), passion flower seed oil (INCI: *Passiflora* lincarnata Seed Oil), avocado seed oil (INCI: *Persea Gratissima* (Avocado) Oil), canola oil (INCI: Canola Oil), argan oil (INCI: Argania *Spinosa* Kernel Oil), rice oil (INCI: *Oryza sativa* seed oil), shea butter (INCI: Butyrospermum Parkii Butter), shea butter ethyl esters (INCI: Shea butter ethyl esters), cocoa butter (INCI: *Theobroma Cacao* (Cocoa) Seed Butter), cetyl alcohol (INCI: Cetyl Alcohol), decyl esters of hydrogenated olive oil (INCI: Hydrogenated Olive Oil Decyl Esters), isododecane (INCI: Isododecane), isopropyl isostearate (INCI: Isopropyl isostearate), squalane (INCI: Squalane), dimethicone (INCI: Dimethicone), dioctyl carbonate (INCI: Dicaprylyl Carbonate), a mixture of caprylic/capric acid triglycerides (INCI: Caprylic/Capric Triglyceride), erucic acid oleyl ester (INCI: Oleyl erucate), a mixture of cetyl and stearyl alcohol (INCI: Cetearyl alcohol), pentaerythritol tetraisostearate (INCI: Pentaerythritol Tetraisostearate), mixture of tridecane (INCI: Tridecane, CAS: 629-50-5) and undecane (INCI: Undecane, CAS: 1120-21-4), pentaerythritol distearate (INCI: Pentaerythrityl Distearate), polydecene (INCI: Polydecene), 1,1,1,3,5,5,5-heptamethyl-3-octyltrisiloxane (INCI: 1,1,1,3,5,5,5-Heptamethyl-3-octyltrisiloxane, CAS: 17955-88-3), Sacha Inchi seed oil (INCI: *Plukenetia Volubilis* Seed Oil), a mixture of high molecular weight silicone elastomers (INCI: Dimethicone Crosspolymer) in low viscosity dimethicone (INCI: Dimethicone), oil flower extracts (INCI: *Glycine Soja* (Soybean) Oil), of common peony flower, Japanese cherry flower, bitter orange flower, true lavender flower, elderberry flowers and damask rose flowers (INCI: *Jasminum officinale* (Jasmine) Flower Extract (i) *Paeonia officinalis* Flower Extract (i) *Prunus serrulata* Flower Extract (i) Citrus aurantium *amara* (Bitter orange) Flower Extract (i) *Lavandula angustifolia* (Lavender) Flower Extract (i) *Sambucus nigra* Flower Extract (i) *Rosa damascena* Flower Oil), a mixture of benzoic acid C12-15-alkyl esters (INCI: C12-15 Alkyl Benzoate) dioctyl ether (CAS: 629-82-3; INCI: Dicaprylyl Ether), candelilla wax (INCI: Candelilla Cera)), triethylhexanoin (INCI: Triethylhexanoin), a mixture of C15-C19 alkanes (INCI: C15-19 Alkane) castor oil (INCI: Castor Oil), hydrogenated castor oil (INCI: Hydrogenated Castor oil), a mixture of castor oil and hydrogenated castor oil (INCI: *Ricinus Communis* (Castor) Seed Oil, Hydrogenated Castor Oil) and their mixtures additional cosmetically active substances (such as, among others: tocopherol (INCI: Tocopherol), tocopherol acetate (INCI: Tocopherol acetate), *spirulina* (INCI: *Spirulina*), palmitoyl-tripeptide-5 (INCI: Palmitoyl Tripeptide-5), a mixture of soybean seed extract and ceramides (INCI: *Glycine* soybean (Soybean) Seed Extract & Ceramide NG), fermentation products of probiotic fraction of *Lactobacillus pentosus*, natural ceramides, mixture of colloidal gold and acetyl-heptapeptide-9 (INCI: Acetyl heptapeptide-9, Colloidal gold), allatoin (INCI: Allantoin), d-panthenol (INCI: D-Panthenol), Indian pennywort extract (INCI: *Centella Asiatica* Extract), rose hydrolate, ascorbyl tetraisopalmitate (INCI: Ascorbyl Tetraisopalmitate), sunflower seed oil (INCI: *Helianthus Annuus* (Sunflower) Seed Oil), betaine (INCI: Betaine), golden algae extract (INCI: *Laminaria Ochroleuca* Extract), nicotinic acid amide (INCI: Niacinamide), rainbow algae extract (INCI: Cystoseira Tamariscifolia Extract), and mixtures thereof), fragrance compositions, other additives, e.g. pH adjusting agents (such as citric acid, sodium carbonate and mixtures thereof, among others), chelating agents (for example, sodium salt of phytic acid (CAS: 17211-15-3), or dyes (for example, chlorophyll copper complex).

All of the indicated additional ingredients of the cosmetic base or product can be respectively used alone or in the form of mixtures with excipients, for example, in the form of commercially available preparations.

A person skilled in the art understands that the above-mentioned ingredients do not limit the scope of the invention in any way, and the above-mentioned cosmetic bases or cosmetic products may comprise both other compounds/ingredients belonging to the above-mentioned groups that are not mentioned above, as well as ingredients belonging to other not mentioned above groups typically added to cosmetic products and cosmetic bases.

In a preferred embodiment of the invention, said cosmetic product preferably comprises:

about 0.10 to about 10.00% by weight, of at least one humectant, preferably about 2.00 to about 10.00% by weight, more preferably about 3.00 to about 10.00% by weight, even more preferably about 5.00 to about 10.00% by weight, for example about 2.00 to about 4.00% by weight, in particular about 3.00 to about 5.00% by weight, particularly preferably about 0.10 to about 1.00% by weight about 0.20 to about 1.50% by weight, of at least one preservative, preferably about 0.50 to about 1.50% by weight, more preferably about 1.00 to about 1.50% by weight, even more preferably about 0.20 to about 0.60% by weight, for example, about 1.00 to about 1.50% by weight, in particular about 0.50 to about 1.00% by weight from about 0.10 to about 3.50% by weight, of at least one thickening agent, preferably from about 0.50 to about 3.50% by weight, more preferably from about 1.50 to about 3.50% by weight, even more preferably from about 0.10 to about 0.50% by weight, for example from about 0.10 to about 0.20% by weight, in particular from about 0.50 to about 1.50% by weight about 2.50 to about 10.00% by weight, of at least one emulsifier, preferably about 2.50 to about 5.50% by weight, more preferably about 2.50 to about 5.00% by weight, even more preferably about 2.50 to about 4.50% by weight, for example about 3.50 to about 5.50% by weight, in particular about 5.00 to about 10.00% by weight, more particularly about 3.00 to about 5.00% by weight about 10.00 to about 35.00% by weight, of at least one emollient, preferably about 15.00 to about 35.00% by weight, more preferably about 30.00 to about 35.00% by weight, even more preferably about 10.00 to about 15.00% by weight, for example about 15.00 to about 25.00% by weight, about 0.10 to about 1.50% by weight of the composition of the invention about 0.10 to about 10.00% by weight, of additional cosmetically active preferably about 2.00 to about 10.00% by substances, weight, more preferably about 5.00 to about 10.00% by weight, even more preferably about 1.00 to about 3.00% by weight, for example about 1.00 to about 2.00% by weight, in particular about 2.00 to about 3.00% by weight about 0.20 to about 0.50% by weight, of optional fragrance composition preferably about 0.30 to about 0.50% by weight, more preferably about 0.20 to about 0.40% by weight, about 0.05 to about 1.00% by weight, of at least one additive, preferably about 0.20 to about 1.00% by weight, more preferably about 0.20 to about 6.00% by weight, even more preferably about 0.05 to about 0.15% by weight, about 10.00 to about 15.00% by weight of optional UV filter and up to 100% by weight of water.

As an additive, a cosmetic product may comprise an ingredient selected from a group comprising at least one pH adjusting agent and at least one chelating agent.

The pH adjusting agent can be preferably present in the cosmetic product in an amount of about 0.05 to about 1% by weight, more preferably about 0.1 to about 0.5% by weight based on the total weight of the cosmetic product.

The chelating agent can be preferably present in the cosmetic product in an amount of about 0.05 to about 1.00% by weight based on the total weight of the cosmetic product.

Cosmetic products and cosmetic bases according to the invention can be manufactured by any method known in the field of the invention.

Cosmetic products and cosmetic bases according to the invention can, in particular, be manufactured by a method including:

a) preparing an aqueous phase and heating it to an elevated temperature,
b) preparing an oil phase and heating it to an elevated temperature,
c) adding an emulsifier to the oil phase and mixing,
d) adding the aqueous phase to the oil phase and homogenizing resulting mixture,
e) optionally cooling the resulting mixture and adding a UV filter,
f) cooling the resulting mixture,
g) adding cosmetically active ingredients, a preservative and optionally a fragrance composition, and then homogenizing the resulting mixture,
h) further cooling the resulting mixture.

The elevated temperature used in steps a) and b) ensures that the ingredients of the oil phase are thoroughly mixed and that the aqueous and oil phase are blended together. Preferably, it ranges from about 70 to about 85° C., more preferably from about 75 to about 80° C., and most preferably it is either 75 or 80° C.

Cooling the mixture in step e) preferably means lowering the temperature of the mixture to about 60° C.

Cooling the mixture in step f) preferably means lowering the temperature of the mixture to a temperature in the range of about 30 to about 40° C., more preferably to a temperature of about 35° C.

Cooling the mixture in step h) preferably means lowering the temperature of the mixture to a temperature in the range of about 20 to about 30° C., more preferably to a temperature of about 25° C.

UV filters are added in step e) to the emulsion produced after mixing the oil and water phases. A person skilled in the art will easily determine the right time to add a given UV filter.

Homogenization of the mixture in the above method can be carried out by any technique used in the field. For example, without limiting the scope of the invention, high-speed homogenization or high-pressure homogenization can be used, as described above with respect to a method of manufacturing the composition according to the invention.

According to the invention, the word "about" used above and below is to be understood as a deviation of +1-5% from the given value, reflecting inaccuracies that may occur during the process of manufacturing of the composition according to the invention, such as during measuring off the composition ingredients.

EXAMPLES

Example 1. Composition According to the Invention

A mixture of vegetable glycerol, bamboo cellulose, magnolol, honokiol, sunflower lecithin, ethylhexylglycerin, hydroxyethylcellulose, potassium sorbate, sodium benzoate and water was prepared and mixed thoroughly. Lecithin was added to the resulting mixture and left to dissolve and hydrate for 24 hours (with stirring). Hydroxyethylcellulose was added to the resulting mixture and mixed (gelation process).

A composition was obtained, having the following ingredients:

| | |
|---|---|
| 10.0% by weight | of vegetable glycerol, |
| 3.0% by weight | of bamboo cellulose |
| 1.0% by weight | of sunflower lecithin, |
| 1.0% by weight | of ethylhexylglycerin, |
| 1.0% by weight | of hydroxyethylcellulose, |
| 1.0% by weight | of magnolol, |
| 1.0% by weight | of honokiol, |
| 0.5% by weight | of potassium sorbate, |
| 0.5% by weight | of sodium benzoate, |
| 81.0% by weight | of water. |

Example 2. Study of Inhibitory Activity Against Tyrosinase

Example 2.1. Assays Carried Out on Microtiter Plates Using a Reader 2.1.1. Equipment and Reagents Used in Assays Carried Out on Microtiter Plates by Using a Reader:

96-well transparent microtiter plates from Brand pure grade

Fluorostar Omega reader (BMG Labtech)

Assay buffer: 50 mM phosphate buffer pH 6.8

Enzyme: tyrosinase (from mushrooms, lyophilized powder, 1000 units/mg, solid, 2.94 mg), CAS 9002-10-2, Sigma T3824-25KU. Enzyme stock solution 2.94 mg per 2 ml of assay buffer. 6-fold diluted enzyme stock solution was used for the assay. Amount of tyrosinase during the assay 1.69 μg Substrate: 3,4-dihydroxy-L-phenylalanine (DOPA, M=197.18 mg/ml), CAS 59-92-7, Sigma D9628-5G. Substrate stock solution 1 mg per 1 ml of 0.15 M phosphoric acid. Substrate concentration during the assay 174.9 μM Solvent for inhibitors: dimethylsulfoxide (DMSO), dimethylformamide (DMF)

2.1.2 Assay Description:

Inhibitor stock solution was prepared—a weighted amount of inhibitor was dissolved in DMSO or DMF (ultrasounds were used additionally for 10 min).

An Eppendorf tube was prepared comprising a mixture: 918 μl of assay buffer, 30 μl of inhibitor solution, 24 μl of enzyme stock solution One test tube comprising a reference mixture (without inhibitor) having the following composition, was prepared: 918 μl of assay buffer, 30 μl of DMSO/DMF solution, 24 μl of enzyme stock solution The test tubes with the mixture were incubated for 30 min at an ambient temperature—the contents were stirred (vortexed) every 10 min.

Three aliquots of the mixture, each having a volume of 280 μl, were taken from each tube and transferred to three wells on a 96-well transparent microtiter plate 10 μl of DOPA substrate stock solution was added to each well with the mixture An increase in absorbance was measured over 5-6 minutes, at wavelength of 475 nm, using a Fluorostar Omega reader (BMG Labtech)

For each well, an increase in absorbance value over time (AA/min) was calculated The degree of enzyme inhibition was expressed as a percentage by dividing the ΔA/min values obtained for mixtures comprising different concentrations of inhibitor by the ΔA/min values for the reference mixture (without inhibitor)

Measurement 1. Inhibitory Activity Assay—Comparison of MAHO, MAHO Base (M. BASE), MAHO Raw Material (M. RAW) Using DMSO as a Solvent In the present assay, three formulations were tested:

MAHO—a mixture of isolated magnolol and honokiol in powder form

MAHO raw material—a composition specified in Example 1, and

MAHO base—a composition specified in Example 1 from which magnolol and honokiol were removed.

A solution of MAHO base and MAHO raw material preparations with the same concentrations was prepared as described in the assay (2.1.2). It was noted that the solubility of MAHO raw material and MAHO base preparations in DMSO was not very good. On the other hand, MAHO dissolved in DMSO very well. A comparison of inhibitory activity is shown in FIG. 1.

Summary of Results:

The MAHO preparation shows inhibitory activity at a concentration of 0.027 mg/290 μl ($9.31\times10^{-5}$ mg/μl) of assay buffer (enzyme activity inhibited to 46%).

Slight inhibition of enzyme activity for MAHO raw material preparation at low concentrations (enzyme activity inhibited to 75% at a concentration of 0.00086 mg/290 μl).

No inhibitory activity of MAHO base was observed.

Example 2.2 Assays Carried Out in Polystyrene Cuvettes Using a Spectrophotometer 2.2.1. Equipment and Reagents Used in Assays 2-8

Brand PS polystyrene cuvettes having a volume of 1.5 ml

Perkin Elmer Lambda EZ201 spectrophotometer

Assay buffer: 50 mM phosphate buffer pH 6.8

Enzyme: tyrosinase (from mushrooms, lyophilized powder, ≥1000 units/mg, solid, 2.94 mg), CAS 9002-10-2, Sigma T3824-25KU. Enzyme stock solution 2.94 mg per 2 ml of assay buffer. 6-fold diluted enzyme stock solution was used for the assay. Amount of tyrosinase during assay 4.9 μg Substrate: 3,4-dihydroxy-L-phenylalanine (DOPA, M=197.18 mg/ml), CAS 59-92-7, Sigma D9628-5G. Substrate stock solution 1 mg per 1 ml of 0.15 M phosphoric acid. Substrate concentration during assay of 88.97 μM (assays 6 and 7) to 97.5 μM (assay 5.1)

Solvent for inhibitors: dimethylsulfoxide (DMSO), dimethylformamide (DMF) The same preparations were used in the assays as for assays in Example 2.1.

For each of the assays, MAHO raw material showed inhibitory properties. Particularly preferred embodiments, having the highest degree of inhibition of enzyme activity, are the examples from assays 2-5 (shown below).

Measurement 2

For measurement 2, a MAHO solution having concentration of 12.88 mg per 129 mg DMSO was used.

Contents of cuvette: 900 μl of assay buffer+20 μl of DMSO/inhibitor+20 μl of enzyme+20 μl of substrate. Incubation took 30 minutes.

A comparison of inhibitory activity for measurement 2 is shown in FIG. 2.

Result: MAHO raw material shows inhibitory properties—enzyme activity inhibited to ~70% at a concentration of $6.5\times10^{-5}$ mg/μl.

Measurement 3

For measurement 3, a MAHO solution having concentration of 58.91 mg per 295 μl in DMSO was used.

Contents of cuvette: 1000 μl of assay buffer+20 μl of DMSO/inhibitor+20 μl of enzyme+20 μl of substrate. Incubation took 30 minutes.

A comparison of inhibitory activity for assay 3 is shown in FIG. 3.

Results: MAHO exhibits inhibitory properties—enzyme activity inhibited to ~50% at a concentration of $5.9\times10^{-5}$ mg/μl and to 88% at a concentration of $5.9\times10^{-6}$ mg/μl.

Measurement 4

For measurement 4, a MAHO solution having concentration of 58.91 mg per 295 μl in DMSO was used.

Contents of cuvette: 1000 μl of assay buffer+50 μl of DMSO/inhibitor+20 μl of enzyme+20 μl of substrate. Incubation took 30 minutes.

A comparison of inhibitory activity for assay 4 is shown in FIG. 4.

Results: MAHO exhibits inhibitory properties—enzyme activity inhibited to ~19% at a concentration of $1.4\times10^{-4}$ mg/μl.

Measurement 5

For measurement 5, the following inhibitor solutions were used: MAHO base at a concentration of 57.48 mg/287 μl in DMSO and MAHO raw material at a concentration of 80.00 mg/400 μl in DMSO Contents of cuvette: 1000 μl of assay buffer+100 μl of DMSO/inhibitor+20 μl of enzyme+20 μl of substrate. Incubation took 30 minutes.

A comparison of inhibitory activity for assay 5 is shown in FIG. 5.

MAHO raw material shows inhibitory properties—enzyme activity inhibited to ~58% at a concentration of 0.017 mg/μl.

MAHO base shows weaker inhibitory properties—enzyme activity inhibited to ~84% at a concentration of 0.017 mg/μl.

Example 3—Day and Night Cream

The ingredients of the aqueous phase (water, propanediol, phytic acid sodium salt) were mixed together and heated to 75° C.

In a separate vessel, the ingredients of the oil phase (passion flower seed oil, oleyl erucinate, dicapric carbonate, carbonic acid ester, caprylic/capric acid triglycerides, shea butter, avocado seed oil and a mixture of cetyl alcohol and stearyl alcohol) were mixed, heated to 75° C., after which emulsifiers (stearoyl glutamate sodium salt, polyglucoside of cetostearyl alcohol, glucose and a mixture of cetyl alcohol/stearyl alcohol were added to the resulting mixture and mixed again.

To the aqueous phase at 75° C. an oil phase of the same temperature was slowly added and homogenized. The resulting mixture was cooled to 60° C., thickeners (carbomer, natural gum arabic (Senegalese) and xanthan gum) were added and homogenized. It was then cooled to 40° C., citric acid and sodium carbonate were added and homogenized again. To the resulting mixture, cosmetically active agents (the composition from Example 1, allantoin, D-panthenol, and Indian pennywort extract) were added sequentially, with the mixture being homogenized after the addition of each active ingredient. To the resulting mixture a mixture of preservatives: Symsave H (hydroxyacetophenone) and Plantservative WSr (Japanese honeysuckle extract, perfoliate honeysuckle flower extract), and a fragrance composition were added. The resulting mixture was homogenized and cooled to 25° C.

A cosmetic composition in the form of a day and night cream was obtained, comprising the following ingredients:

| | |
|---|---|
| 0.30% by weight | of hydroxyacetophenone (Symsave H, Symrise) |
| 0.05% by weight | of allantoin |
| 0.10% by weight | of phytic acid sodium salt (Dermofeel PA-12, Evonik) |
| 0.10% by weight | of natural gum arabic (Senegalese) and xanthan gum (Solagum AX, SEPPIC) |
| 3.00% by weight | of propanediol (Zemea Propanediol, DuPont Tate & Lyle) |
| 0.25% by weight | of carbomer (Carbopol ETD 2050, Lubrizol) |
| 0.12% by weight | of sodium carbonate |
| 0.50% by weight | of sodium stearoyl glutamate (Eumulgin SG, BASF) |
| 3.00% by weight | of polyglucoside of cetostearyl alcohol, glucose, and a mixture of cetyl alcohol and stearyl alcohol (Montanov 68, SEPPIC) |
| 0.20% by weight | of passion flower seed oil |
| 2.00% by weight | of shea butter (Lipex Shea Soft, AAK AB) |
| 3.00% by weight | of caprylic/capric acid triglycerides (Myritol 318, BASF) |
| 1.00% by weight | of carbonic acid ester, dicapryl carbonate (Cetiol CC, BASF) |
| 4.00% by weight | of oleyl erucinate (Cetiol J 600) |

-continued

| | |
|---|---|
| 0.50% by weight | of avocado seed oil |
| 2.50% by weight | of mixture of cetyl alcohol and stearyl alcohol |
| 1.00% by weight | of D-panthenol |
| 1.00% by weight | of Indian pennywort extract |
| 0.20% by weight | of Japanese honeysuckle flower extract, perfoliate honeysuckle flower extract (Plantservative WSr, Campo Research) |
| 0.20% by weight | of citric acid |
| 0.40% by weight | of fragrance composition (day cream 3) |
| 1.00% by weight | of the composition according to Example 1 |
| up to 100% by weight | of water |

Example 4—Night Cream

The ingredients of the aqueous phase (water, propanediol), were mixed together and heated to 75° C. A thickener—hectorite—was added and then homogenized.

In a separate vessel, the ingredients of the oil phase (pentaerythrityl distearate, caprylic/capric acid triglycerides, cocoa butter, shea butter, carbonic acid ester, (dicapryl carbonate), polydecene, decyl esters of hydrogenated olive oil, 1,1,1,3,5,5,5-heptamethyl-3-octyltrisiloxane, squalane, rapeseed oil, avocado seed oil, argan oil, Sacha Inchi seed oil, a mixture of high molecular weight silicone elastomers, and emulsifiers (polyglucoside of cetostearyl alcohol, glucose and a mixture of cetyl alcohol and stearyl alcohol, and glyceryl stearate), and heated to 75° C.

The oil phase at 75° C. was slowly added to the aqueous phase and then homogenized. The resulting mixture was cooled to 30° C., citric acid was added and then homogenized again. Cosmetically active agents (the composition from Example 1, betaine, SK-Influx V, vitamin E acetate, a mixture of soybean seed extract and ceram ides, a mixture of colloidal gold and acetyl-heptapeptide-9) were added sequentially to the resulting mixture, with the mixture being homogenized after the addition of each ingredient. To the resulting mixture a mixture of preservatives: Symsave H (hydroxyacetophenone) and Plantservative WSr, and a fragrance composition were added. The resulting mixture was homogenized and cooled to 25° C.

A cosmetic composition in the form of a night cream comprising the following ingredients, was obtained:

| | |
|---|---|
| 0.50% by weight | of propanediol (Zemea Propanediol, DuPont Tate & Lyle) |
| 1.00% by weight | of betaine (Natural Extract AP) |
| 0.20% by weight | of SK-Influx V |
| 0.50% by weight | of hydroxyacetophenone (Symsave H, Symrise) |
| 0.15% by weight | of hectorite (Hydroclay Bentone 900) |
| 5.00% by weight | of polyglucoside of cetostearyl alcohol, glucose, and a mixture of cetyl alcohol and stearyl alcohol (Montanov 68, SEPPIC) |
| 1.00% by weight | of glyceryl stearate (Cutina KD-16) |
| 0.50% by weight | of pentaerythritol distearate (Cutina PES) |
| 4.00% by weight | of caprylic/capric acid triglycerides (Myritol 318, BASF) |
| 1.00% by weight | of cocoa butter (Lipex Cocoasoft, AAK AB) |
| 2.00% by weight | of shea butter |
| 3.00% by weight | of carbonic acid ester and dicapryl carbonate (Cetiol CC, BASF) |
| 4.00% by weight | of polydecene (Nexbase 2008) |
| 2.00% by weight | of decyl esters of hydrogenated olive oil (Phytowax Olive 10 L 40, Sophim) |
| 3.00% by weight | of 1,1,1,3,5,5,5-heptamethyl-3-octyltrisiloxane (Silsoft 034, Momentive) |
| 4.00% by weight | of squalane (Pripure 3759, Croda) |
| 4.00% by weight | of canola oil |
| 2.00% by weight | of avocado seed oil |
| 0.10% by weight | of Sacha Inchi (Inchol) seed oil |
| 0.10% by weight | of argan oil |
| 1.00% by weight | of vitamin E acetate |
| 0.10% by weight | of mixtures of soybean seed extract and ceramides (Hydromide Blend) |
| 1.50% by weight | of a mixture of high molecular weight silicone elastomers (INCI: Dimethicone Crosspolymer) in low viscosity dimethicone, (INCI: Dimethicone), (DC 9041, DOW CHEMICAL) |
| 0.20% by weight | of Japanese honeysuckle flower extract, perfoliate honeysuckle flower extract (Plantservative WSr, Campo Research) |
| 1.00% by weight | of the composition according to Example 1 |
| 0.01% by weight | of a mixture of colloidal gold and acetyl-heptapeptide-9 (MVP Golden Collagenine, Infitec) |
| 0.07% by weight | of citric acid |
| 0.35% by weight | of fragrance composition (day cream 3) |
| up to 100.00% by weight | of water |

Example 5—Eye Cream

The ingredients of the aqueous phase (water, glycerol, phytic acid sodium salt) were mixed together and heated to 75° C.

In a separate vessel, the ingredients of the oil phase (ethyl esters of shea butter, isopropyl isostearate, pentaerythrityl tetraisostearate, rice oil, a mixture of tridecane and undecane) were mixed, emulsifiers (Polyglucoside of cetostearyl alcohol, glucose and a mixture of cetyl alcohol and stearyl alcohol, cetyl phosphate potassium salt) were added and heated to 75° C. and stirred.

The oil and water phases were combined at 75° C. and homogenized. The resulting mixture was cooled to 35° C., citric acid was added and then homogenized again. Cosmetically active agents (the composition from Example 1, rose hydrolate, a mixture of soybean seed extract and ceram ides, vitamin E acetate, ascorbyl tetraisopalmitate and palmitoyl-tripeptide-5) were added sequentially to the resulting mixture, with the mixture being homogenized after the addition of each active ingredient. To the resulting mixture a thickener—sodium carbomer was added, followed by homogenizing. A mixture of Symsave H (hydroxyacetophenone) and Plantservative WSr was added to the resulting mixture, along with a fragrance composition. The resulting mixture was homogenized and cooled to 25° C.

A cosmetic composition in the form of an under-eye cream, having the following ingredients was obtained:

| | |
|---|---|
| 5.00% by weight | of rose hydrolate |
| 3.00% by weight | of glycerol |
| 0.05% by weight | of phytic acid sodium salt (Dermofeel PA-12, Evonik) |
| 0.60% by weight | of hydroxyacetophenone (Symsave H, Symrise) |
| 5.00% by weight | of polyglucoside of cetostearyl alcohol, glucose, and a mixture of cetyl alcohol and stearyl alcohol (Montanov 68, SEPPIC) |
| 0.25% by weight | of cetyl phosphate potassium salt (Amphisol K, DSM) |
| 2.00% by weight | of ethyl esters of shea butter (Lipex Shealight, AAK AB) |
| 4.50% by weight | of isopropyl isostearate (Prisorine 2021) |
| 2.50% by weight | of pentaerythritol tetraisostearate (Prisorine 3631) |
| 1.50% by weight | of rice oil |
| 0.50% by weight | of a mixture of soybean seed extract and ceramides (Hydromide Blend) |
| 0.50% by weight | of vitamin E acetate |
| 0.15% by weight | of ascorbyl tetraisopalmitate (Nikkol VC-IP, Nikko Chemicals) |
| 0.50% by weight | of sodium carbomer (AQUPEC MG N40R, Sumitomo Seika Chemicals). |
| 3.00% by weight | of a mixture of tridecane and undecane (Cetiol Ultimate, BASF) |
| 2.50% by weight | of palmitoyl-tripeptide-5 (Syn-Coll, Natura Siberica) |
| 1.00% by weight | of the composition according to Example 1 |
| 0.20% by weight | of Japanese honeysuckle flower extract, perfoliate honeysuckle flower extract (Plantservative WSr, Campo Research) |
| 0.05% by weight | of citric acid |
| up to 100.00% by weight | of water |

Example 6—Day Cream

The ingredients of the aqueous phase (water, propanediol, glycerol, phytic acid) were mixed together and heated to 80° C. To resulting mixture, the thickeners—magnesium-aluminum silicate and xanthan gum were added, followed by homogenizing.

In a separate vessel, the ingredients of the oil phase (1,6-dibutyl ester of hexanedioic acid, cetyl alcohol, caprylic/capric acid triglycerides, ethyl esters of shea butter, decyl esters of hydrogenated olive oil, oil (soybean oil) extracts of common peony flower, Japanese cherry flower extracts, bitter orange flower extract, true lavender flower extract, elderberry flower extract and damask rose flower extract, avocado seed oil, cyclopentasiloxane dispersion in isododecane) were mixed and heated to 80° C., followed by the addition of emulsifier (cetyl phosphate potassium salt and glyceryl stearate) and mixed. The aqueous phase was then slowly added to the oil phase and the two were combined at 80° C. and homogenized. The resulting mixture was cooled to 60° C., and a UV filter (a mixture of ethylhexyl salicylate, 2,2'-[6-(4-methoxyphenyl)-1,3,5-triazine-2,4-diyl]bis(5-((2-ethylhexyl)oxy)-phenol, 4,4",4"-(1,3,5-triazine-2,4,6-triyltrimino)tris-,tris(2-ethylhexyl)benzoic acid ester and diethylamino-hydroxybenzoylhexyl benzoate) was added and homogenized.

After cooling the mixture to 40° C., cosmetically active agents (the composition from Example 1, tocopherol, vitamin E acetate, *spirulina*, palmitoyl-tripeptide-5) and colorant (chlorophyll copper complex) were added sequentially, with the mixture being homogenized after the addition of each active ingredient. To the resulting mixture, a mixture of Symsave H (hydroxyacetophenone), 1,2-Hydrolite-6 (hexanediol) and Plantservative WSr, citric acid and fragrance composition were added. The resulting mixture was homogenized and cooled to 25° C.

A cosmetic composition in the form of a day cream, having the following ingredients was obtained:

| | |
|---|---|
| 2.00% by weight | of propanediol (Zemea Propanediol, DuPont Tate & Lyle) |
| 0.50% by weight | of hydroxyacetophenone (Symsave H, Symrise) |
| 0.10% by weight | of phytic acid (Dermofeel PA, Evonik) |
| 2.00% by weight | of magnesium-aluminum silicate (Veegum K, Vanderbilt Minerals) |
| 2.00% by weight | of glycerol |
| 0.20% by weight | of xanthan gum (Keltrol, CP Kelco) |
| 2.50% by weight | of cetyl phosphate potassium salt (Amphisol K, DSM) |
| 4.50% by weight | of ethylhexyl salicylate (Eusolex OS, Merck) |
| 7.00% by weight | of 1,6-dibutyl ester of hexanedioic acid (Cetiol B, BASF) |
| 1.80% by weight | of cetyl alcohol |
| 2.00% by weight | of 2,2'-[6-(4-methoxyphenyl)-1,3,5-triazine-2,4-diyl]bis(5-((2-ethylhexyl)oxy)-phenol (Tinosorb S, BASF) |
| 2.00% by weight | of 4,4',4"-(1,3,5-triazine-2,4,6-triyltrimino)tris-, tris(2-ethylhexyl)ester of benzoic acid (Uvinul T 150, BASF) |
| 3.00% by weight | of caprylic/capric acid triglycerides (Myritol 318, BASF) |
| 2.00% by weight | of diethylamino-hydroxybenzoyl-hexyl benzoate (Uvinul A Plus, BASF) |
| 3.00% by weight | of ethyl esters of shea butter (Lipex Shea Light, AAK AB) |
| 2.00% by weight | of glyceryl stearate (CUTINA GMS, BASF) |
| 0.50% by weight | of decyl esters of hydrogenated olive oil (Phytowax Olive 10 L 40, Sophim) |
| 1.00% by weight | of oil (soybean oil) common peony flower extract, Japanese cherry flower extract, bitter orange flower extract, true lavender flower extract, elderberry flower extract and damask rose flower extract, (Midsummer Night's Dream Oil, Croda) |
| 1.00% by weight | of avocado seed oil |
| 0.05% by weight | of tocopherol (Cosphaderm T-70 NON GMO). |
| 2.50% by weight | of cyclopentasiloxane dispersion in isododecane (Gransil PC-12, Grant Industries) |
| 0.80% by weight | of vitamin E acetate |
| 0.70% by weight | of 1,2-hexanediol (Hydrolite-6, Symrise) |
| 0.08% by weight | of Japanese honeysuckle flower extract, perfoliate honeysuckle flower extract (Plantservative WSr, Campo Research) |
| 1.00% by weight | of the composition according to Example 1 |
| 0.05% by weight | of spirulina |
| 0.015% by weight | of citric acid |
| 0.015% by weight | of chlorophyll copper complex |
| 0.50% by weight | of palmitoyl-tripeptide-5 (Syn-Coll, Natura Siberica) |
| 0.40% by weight | of fragrance composition (day cream 3) |
| up to 100.00% by weight | of water |

Example 7—Facial Serum

The ingredients of the aqueous phase (water, propanediol, glycerol, sodium salt of phytic acid) were mixed together and heated to 75° C.

In a separate vessel, the ingredients of the oil phase (cetyl alcohol, shea butter, isopropyl isostearate, squalane, dimethicone, carbonic acid ester, dicapryl carbonate, argan oil, passion flower seed oil) were mixed, emulsifiers (glyceryl stearate citrate, stearoyl glutamate sodium salt, glyceryl stearate, mixture of C14-C22 alcohols, C12-C20 alkyl glucosides) were added and heated to 75° C. To the resulting mixture a thickener—hectorite modified with stearalkonium salt was added, followed by homogenizing.

The oil phase was then slowly and gradually added to the aqueous phase and combined at 75° C. and homogenized. The resulting mixture was cooled to 35° C., citric acid was added and then homogenized. The active ingredients (the composition from Example 1, tocopherol, a mixture of soybean seed extract and ceram ides, fermentation products of the probiotic fraction of *Lactobacillus pentosus* and a mixture of colloidal gold and acetyl-heptapeptide-9) were added to the resulting mixture, followed by homogenizing the mixture. To the resulting mixture preservatives (hydroxyacetophenone and Japanese honeysuckle extract, perfoliate honeysuckle flower extract), as well as a fragrance composition were added. The resulting mixture was homogenized again and cooled to 25° C.

A cosmetic composition in the form of a facial serum, having the following ingredients was obtained:

| | |
|---|---|
| 0.10% by weight | of phytic acid sodium salt (Dermofeel PA-12, Evonik) |
| 0.50% by weight | of hydroxyacetophenone (Symsave H, Symrise) |
| 4.00% by weight | of propanediol (Zemea Propanediol, DuPont Tate & Lyle) |
| 3.00% by weight | of glycerol |
| 2.00% by weight | of glyceryl stearate citrate (AXOL C62, Evonik) |
| 1.00% by weight | of a mixture of C14-C22 alcohols, C12-C20 alkyl glucosides (MONTANOV L, SEPPIC) |
| 1.50% by weight | of cetyl alcohol |
| 0.80% by weight | of glyceryl stearate (CUTINA GMS, BASF) |

-continued

| | |
|---|---|
| 1.50% by weight | of shea butter (Lipex Shea Soft, AAK AB) |
| 3.00% by weight | of isopropyl isostearate (Prisorine 2021) |
| 2.00% by weight | of squalane (Pripure 3759, Croda) |
| 2.00% by weight | of dimethicone (ABIL 350, Evonik) |
| 1.00% by weight | of hectorite modified with stearalkonium salt (COSMEDIA GEL CC, BASF) |
| 2.00% by weight | of carbonic acid ester, dicapryl carbonate (Cetiol CC, BASF) |
| 0.10% by weight | of tocopherol (Cosphaderm T-70 NON GMO). |
| 1.00% by weight | of argan oil |
| 0.50% by weight | of passion flower seed oil |
| 0.10% by weight | of a mixture of soybean seed extract and ceramides (Hydromide Blend) |
| 0.20% by weight | of Japanese honeysuckle flower extract, perfoliate honeysuckle flower extract (Plantservative WSr, Campo Research) |
| 0.05% by weight | of citric acid |
| 0.20% by weight | of probiotic fermentation products of *Lactobacillus pentosus* fraction (BIOTILYS, Greentech) |
| 0.15% by weight | of a mixture of colloidal gold and acetyl-heptapeptide-9 (MVP Golden Collagenine, Infitec) |
| 1.00% by weight | of the composition according to Example 1 |
| 0.35% by weight | of fragrance composition (day cream 3) |
| up to 100.00% by weight | of water |

Example 8—Natural Cream for Mature Skin

The ingredients of the aqueous phase (water, propanediol, glycerol) were mixed together and heated to 75° C. In a separate vessel, the oil phase ingredients (a mixture of cetyl and stearyl alcohol, a mixture of castor oil and hydrogenated castor oil, canola oil, shea butter, caprylic/capric acid triglycerides, carbonic acid ester, dicapric carbonate, oleyl erucate, a mixture of C15-C19 alkanes) were mixed, emulsifiers (stearoyl glutamate sodium salt, glyceryl stearate) were added and heated to 75° C. To the resulting mixture a thickener—*sclerotium* gum was added, followed by homogenizing.

The oil phase was then slowly and gradually added to the aqueous phase and combined at 75° C. and homogenized. The resulting mixture was cooled to 35° C., citric acid was added and then homogenized. Active ingredients (the composition from Example 1) were added to the resulting mixture, followed by homogenizing the mixture. Preservatives (sodium benzoate, potassium sorbate) were added to the resulting mixture. The resulting mixture was homogenized again and cooled to 25° C.

A cosmetic composition in the form of a natural cream for mature skin, having the following ingredients was obtained:

| | | |
|---|---|---|
| 2.00% | by weight | of propanediol (Zemea Propanediol, DuPont Tate & Lyle) |
| 0.10% | by weight | of sclerotium gum (AMIGUM ECO, Alban Muller) |
| 3.00% | by weight | of glycerol |
| 1.00% | by weight | of sodium stearoyl glutamate (Eumulgin SG, BASF) |
| 1.00% | by weight | of glyceryl stearate (CUTINA GMS, BASF) |
| 3.70% | by weight | of a mixture of cetyl and stearyl alcohol |
| 1.00% | by weight | of a mixture of castor oil and hydrogenated castor oil (CASTROLATUM, Aston Chemicals) |
| 1.50% | by weight | of canola oil |
| 3.00% | by weight | of shea butter (Lipex Shea Soft, AAK AB) |
| 3.00% | by weight | of caprylic/capric acid triglycerides (Myritol 318, BASF) |
| 3.00% | by weight | of carbonic acid ester, dicapryl carbonate (Cetiol CC, BASF) |
| 3.00% | by weight | of oleyl erucinate (Cetiol J 600) |
| 2.00% | by weight | of a mixture of C15-C19 alkanes (EMOGREEN L14, Seppic) |
| 0.35% | by weight | of citric acid |
| 1.00% | by weight | of the composition according to Example 1 |
| 1.20% | by weight | of a mixture of sodium benzoate and potassium sorbate |
| up to 100.00% | by weight | of water |

Example 9— Application Testing 9.1 Testing of a natural cream

Using a natural cream (Example 8), an application testing was conducted with 14 people of the age from 41 to 70 (including 14 people in the instrumental test). The test was completed by 14 people.

TABLE 1

Skin types of the female participants of the applied research

| Skin type | % of respondents |
|---|---|
| sensitive | 71% |
| normal | 7% |
| greasy | 0% |
| mixed | 50% |
| vascular | 50% |
| dry | 21% |

The test was divided into two parts—an instrumental test and a questionnaire survey.

Instrumental Test

Each female participant in the test received a container with a cream and instructions for use. According to these instructions, a small amount of the cream is applied to the face. The cream was to be used twice a day, both day and night for 4 weeks. During the indicated period, the female participants used about 50 grams of the tested cream.

Before the application of the tested product (pre-test) and after 4 weeks (end of the test), instrumental tests (color—melanin and erythema, number of spots and UV spots) were performed using the appropriate apparatus (manufactured by Courage-Khazaka and Canfield) according to the procedures of the In Vivo Testing Laboratory.

With respect to the described tests, the following definitions apply:

The term "number of features" means the number of features (changes) regardless of their size or intensity. This parameter can be used to track the progress of treatment, in which the criterion is a reduction in the frequency of occurrence of a particular feature.

The term "result" refers to the full information about the effect of a feature on the client's skin. "Result" analyzes the total size and area, as well as the intensity of occurrence of the analyzed feature. This parameter can be used when the size and intensity of the feature are the most relevant indicators of treatment effectiveness.

The term "actual improvement" refers to the number of female participants in the test (expressed in %) who experienced a preferable change (in this case, a reduction in melanin amount) compared to day "0," that is the day the study began.

Questionnaire Survey

After the test was completed, the care properties of the tested product, as well as the subjective impressions of the female participants were evaluated by a questionnaire.

Test Results

The test results are shown in Tables 2-7 below.

TABLE 2

Instrumental test results - effect of the tested natural cream on skin tone, skin hydration, firmness and elasticity (Cutometer- MPA- 580)

| Parameter | number of female participants | before | improvement after 4 weeks of the test in the whole group | improvement after 4 weeks of the test in female participants with actual improvement |
|---|---|---|---|---|
| hydration | 14 | 100% | 107% | 124% in 64% of respondents |
| tone- melanin | | | 81% (reduction by 19%) | 81% (reduction by 19%) in 100% of respondents |
| tone - erythema (erythema) | | | 89% (reduction by 11%) | 86% (reduction in redness of 14%) in 86% of respondents |
| firmness | | | 125% | 138% in 79% of respondents |
| flexibility | | | no improvement | no improvement in min 50% of respondents |

TABLE 3

Instrumental test results - effect of the tested natural cream on skin smoothness (visioscan)

| Parameters characterizing skin smoothness | number of respondents | before the test | improvement in the entire group after 4 weeks of use. | actual improvement |
|---|---|---|---|---|
| Ser- epidermal roughness | 13 | 100% | no improvement | 70% (reduction of epidermal roughness of 30%) in 54% of respondents |
| Sesm- smoothness including hydration | | | 106% | 128% in 62% of respondents |
| SEw- number of wrinkles in different planes | | | no improvement | no improvement in min. 50% of respondents |
| Surface- the degree of skin smoothness | | | no improvement | no improvement in min. 50% of respondents |
| Volum- depth, volume and number of depressions and wrinkles | | | no improvement | no improvement in min. 50% of respondents |

The table above shows mean data for the entire group of female participants in the test.

9.2 Tests on Cosmetic Products According to Examples 3, 4, 5 and 7

TABLE 4

| Skin type of test participants | | | | |
|---|---|---|---|---|
| | Day/night cream | Night cream | Under-eye cream | Face serum |
| | Number of female respondents | | | |
| | 24 | 25 | 24 | 25 |
| skin type | % of respondents | | | |
| sensitive | 75% | 88% | 79% | 79% |
| normal | 0% | 8% | 0% | 0% |
| greasy | 4% | 4% | 0% | 0% |
| hyperreactive | 17% | 12% | 17% | 8% |
| mixed | 63% | 48% | 38% | 29% |
| vascular | 38% | 60% | 75% | 71% |
| dry | 38% | 28% | 46% | 50% |
| allergic | 17% | 24% | 33% | 21% |

TABLE 5

| Adverse effects occurring in respondents | | | | |
|---|---|---|---|---|
| | Day/night cream | Night cream | Under-eye cream | Face serum |
| | Number of female respondents | | | |
| | 24 | 25 | 24 | 25 |
| Adverse effects | % of respondents | | | |
| burning, irritation of eyes/eye-sockets | 0% | 0% | 4% | 0% |
| tearing of the eyes | 0% | 4% | 4% | 0% |
| irritation of the skin around the eyes | 0% | 0% | 0% | 0% |
| dry skin sensation | 4% | 0% | 0% | 0% |
| skin tightness sensation | 4% | 0% | 0% | 8% |
| flaking of the skin | 0% | 0% | 0% | 4% |
| burning and stinging skin sensation | 0% | 0% | 0% | 0% |
| rash | 0% | 0% | 0% | 0% |
| skin redness | 0% | 0% | 0% | 8% |
| skin itching | 0% | 0% | 0% | 0% |
| whiteheads, blackheads | 4% | 0% | 0% | 0% |
| urticarial blisters | 0% | 0% | 0% | 0% |
| overall discomfort | 0% | 0% | 4% | 0% |
| none of the above | 88% | 96% | 92% | 88% |

TABLE 6

| Instrumental test results - effect of tested cosmetic products on skin tone, skin hydration, firmness and elasticity (Cutometer- MPA- 580) | | | | | | | | | |
|---|---|---|---|---|---|---|---|---|---|
| parameters characterizing | | Face serum (n = 11) | | Day and night cream (n = 13) | | Under-eye and eyelid cream (n = 12) | | Night cream | |
| the overall condition of the skin | before the test | improvement across the group | actual improvement | improvement across the group | actual improvement | improvement across the group | actual improvement | improvement across the group | actual improvement |
| tone- melanin | 100% | 90% | 81% (skin brightening by 19%) in 64% of respondents | 98% | 85% (skin brightening by 15%) in 54% of respondents | 81% (skin brightening by 19%) | skin brightening by 32% in 67% of respondents | NT | NT |
| tone- degree of skin redness | | no improvement | no improvement in min. 50% of respondents | no improvement | no improvement in min. 50% of respondents | no improvement | no improvement in min. 50% of respondents | NT | NT |
| the degree of hydration of the skin | | no improvement | no improvement in min. 50% of respondents | 115% | 135% in 69% of respondents | no improvement | improvement by 17% in 50% of respondents | NT | NT |
| skin firmness | | no improvement | no improvement in min. 50% of respondents | no improvement | no improvement in min. 50% of respondents | NT | NT | no improvement | no improvement in min. 50% of respondents |
| skin elasticity | | 106% | 118% in 64% of respondents | no improvement | 116% in 62% ofrespondents | NT | NT | no improvement | no improvement in min. 50% of respondents |

NT—not tested

TABLE 7

Instrumental test results - effect of tested cosmetic products on skin smoothness (visioscan)

| Parameters characterizing skin smoothness, n = 13 | before | Day/night cream: Improvement across the group | Day/night cream: Actual improvement | Night cream: Improvement across the group | Night cream: Actual improvement | Under-eye cream: Improvement across the group | Under-eye cream: Actual improvement | Face serum: Improvement across the group | Face serum: Actual improvement |
|---|---|---|---|---|---|---|---|---|---|
| NRJ - overall skin condition | 100% | no improvement | 109% (improvement in overall skin condition by 9% in 62% of respondents) | no improvement | 119% in 58% of respondents | n/b* | n/b | n/b* | n/b |
| Sesm-smoothness including hydration | | 118% | 168% (improvement in skin smoothness by 68%) in 54% of respondents | n/b* | n/b | 117% | increase in smoothness by 31% in 75% of respondents | n/b* | n/b |
| SEw - number of wrinkles in different planes | | no improvement | 79% (reduction in number of wrinkles by 21%) in 54% of respondents | no improvement | 69% (reduction in number of wrinkles by 31%) in 50% of respondents | NT | NT | 99% | 75% (reduction in number of wrinkles by 25%) in 55% of respondents |
| Volume - depth, volume and number of depressions and wrinkles | | 96% | 68% (reduction in depth, volume and number of depressions and wrinkles by 32%) in 54% of respondents | 95% | 72% (reduction in depth, volume and number of depressions and wrinkles by 28%) in 50% of respondents | NT | NT | NT | NT |
| Corner Density - skin cross-linking | | no improvement | 112% (improvement in skin cross-linking by 12%) in 54% of respondents | no improvement | 116% (improvement in skin cross-linking by 12%) in 58% of respondents | 106% | improvement in skin cross-linking by 15% in 67% of respondents | no improvement | 107% in 55% of respondents |
| Ser-epidermal roughness | | NT | NT | NT | NT | 80% (reduction by 20%) | reduction of epidermal roughness by 37% in 75% of respondents | 88% | no improvement in min. 50% of respondents |
| Sesc-flaking including hydration value | | NT | NT | NT | NT | n/b* | n/b | 98% | 73% in 55% of respondents |
| Anisotropy Index - the appearance of skin texture | | NT | NT | NT | NT | 100% | improvement in the appearance of skin texture by 2% in 58% of respondents | NT | NT |

*NT—not tested

TABLE 8

Instrumental test results - effect of tested cosmetic products on skin smoothness (VISIA)

| type of measurement | | Before the test | Day/night cream n = 13 | | Night cream n = 12 | | Under-eye cream n = 12 | | Face serum n = 11 | |
|---|---|---|---|---|---|---|---|---|---|---|
| wrinkles | number of features | 100% | 99% | 76% in 54% of respondents | no improvement | 86% in 50% of respondents | no improvement | no improvement in min 50% of respondents | 83% | 66% in 55% of respondents |
| | result | | 93% | 78% in 69% of respondents | no improvement | no improvement in min. 50% of respondents | no improvement | reduction by 11% in 50% of respondents | no improvement | no improvement in min. 50% of respondents |

TABLE 8-continued

Instrumental test results - effect of tested cosmetic products on skin smoothness (VISIA)

| type of measurement | | Before the test | Day/night cream n = 13 | | Night cream n = 12 | | Under-eye cream n = 12 | | Face serum n = 11 | |
|---|---|---|---|---|---|---|---|---|---|---|
| inequalities | number of features | | no improvement | no improvement in min. 50% of respondents | 98% | no improvement in min. 50% of respondents | | | no improvement | no improvement in min. 50% of respondents |
| | result | | no improvement | no improvement in min. 50% of respondents | no improvement | no improvement in min. 50% of respondents | | | no improvement | no improvement in min. 50% of respondents |
| spots | number of features | | no improvement | no improvement in min. 50% of respondents | no improvement | 93% in 58% of respondents respondents | | | no improvement | no improvement in min. 50% of respondents |
| | result | | no improvement | no improvement in min. 50% of respondents | no improvement | 94% in 58% of respondents respondents | | | no improvement | no improvement in min. 50% of respondents |
| UV spots | number of features | | no improvement | no improvement in min. 50% of respondents | no improvement | 97% in 50% of respondents respondents | | | 98% | 93% in 55% of respondents respondents |
| | result | | no improvement | no improvement in min. 50% of respondents | 96% | 89% in 50% of respondents respondents | | | no improvement | no improvement in min. 50% of respondents |
| Red areas | number of features | | no improvement | no improvement in min. 50% of respondents | 91% | 78% in 58% of respondents respondents | | | no improvement | no improvement in min. 50% of respondents |
| | result | | 99% | 89% in 54% of respondents | no improvement | 93% in 58% of respondents | | | no improvement | no improvement in min. 50% of respondents |

The invention claimed is:

1. A cosmetic composition comprising:

0.5 to 20.0% by weight of glycerol, 0.3 to 13.00% by weight of thickening agent selected from the group consisting of cellulose, hydroxyethylcellulose and their mixtures, 0.5 to 5.00% by weight of lecithin, 0.5 to 10.00% by weight of ethylhexylglycerin, a cosmetically active ingredient, wherein the cosmetically active ingredient consists of 0.1 to 10.00% by weight of magnolol or its cosmetically acceptable derivative selected from among salt, solvate or hydrate, and 0.1 to 10.00% by weight of honokiol or its cosmetically acceptable derivative selected from among salt, solvate or hydrate, 0.5 to 1.00% by weight of at least one preservative selected from the group consisting of potassium sorbate, sodium benzoate and their mixtures, and up to 100% by weight of water, wherein the percentages are expressed in relation to the total weight of the composition.

2. The composition according to claim 1, characterized in that it comprises 10.0% by weight of glycerol, 3.0% by weight of cellulose, 1.0% by weight of lecithin, 1.0% by weight of ethylhexylglycerin, 1.0% by weight of hydroxyethylcellulose, 1.0% by weight of magnolol, 1.0% by weight of honokiol, 0.5% by weight of potassium sorbate, 0.5% by weight of sodium benzoate, and 81.0% by weight of water, wherein the percentages are expressed in relation to the total weight of the composition.

3. The composition according to claim 1, characterized in that it comprises magnolol and honokiol in the form of an extract comprising a concentration of about 90 to about 98% by weight of active ingredient.

4. The composition according to claim 1, characterized in that it comprises magnolol and honokiol in an isolated form.

5. A cosmetic product characterized in that it comprises 0.10-10.00% by weight of at least one humectant, 0.20-3.00% by weight of at least one preservative, 0.10-5.00% by weight of at least one thickening agent, 2.50-10.00% by weight of at least one emulsifier, 10.00-35.00% by weight of at least one emollient, 0.10-1.50% by weight of the composition as defined in claim 1, 0.10-10.00% by weight of additional cosmetically active substances, 0.05-1.00% by weight of at least one additive, and up to 100% by weight of water, in relation to the total weight of the cosmetic product.

6. The cosmetic product according to claim 5, characterized in that it additionally comprises 0.20-0.50% by weight of a fragrance composition.

7. The cosmetic product according to claim 5, characterized in that it comprises 10.00 to 15.00% by weight of at least one UV filter.

8. The cosmetic product according to claim 5, characterized in that it is selected from the group consisting of emulsions, in the form of a cream, including day cream, night cream, under-eye and eyelid cream, and facial natural cream, lotion, milk and serum.

9. The cosmetic product according to claim 5, characterized in that it is in the form of a day and night cream, and comprises:

2.00-4.00% by weight of at least one humectant, 0.20-0.60% by weight of at least one preservative, 0.10-0.50% by weight of at least one thickening agent, 2.50-4.50% by weight of at least one emulsifier, 10.00-15.00% by weight of at least one emollient, 0.50-1.50% by weight of the composition as defined in claim 1, 1.00-3.00% by weight, of at least one additional cosmetically active substance, 0.30-0.50% by weight of fragrance composition, 0.20-0.60% by weight of at least one additive, and up to 100% by weight water in relation to the total weight of the cosmetic product.

10. The cosmetic product according to claim 5, characterized in that it is in the form of a night cream, and comprises:

| | | |
|---|---|---|
| 0.10-1.00% | by weight | of at least one humectant, |
| 0.50-1.00% | by weight | of at least one preservative, |
| 0.10-0.20% | by weight | of at least one thickening agent, |
| 5.00-10.00% | by weight | of at least one emulsifier, |
| 30.00-35.00% | by weight | of at least one emollient, |
| 0.50-1.50% | by weight | of the composition as defined in claim 1, |
| 2.00-3.00% | by weight, | of at least one additional cosmetically active substance, |
| 0.20-0.40% | by weight | of fragrance composition, |
| 0.05-1.00% | by weight | of at least one additive, |
| and up to 100% | by weight | of water |

in relation to the total weight of the cosmetic product.

11. The cosmetic product according to claim 5, characterized in that it is in the form of a day cream, and comprises:

| | | |
|---|---|---|
| 3.00-5.00% | by weight | of at least one humectant, |
| 1.00-1.50% | by weight | of at least one preservative, |
| 1.50-3.50% | by weight | of at least one thickening agent, |
| 3.50-5.50% | by weight | of at least one emulsifier, |
| 10.00-15.00% | by weight | of at least one UV filter, |
| 15.00-25.00% | by weight | of at least one emollient, |
| 0.50-1.50% | by weight | of the composition as defined in claim 1, |
| 1.00-2.00% | by weight, | of at least one additional cosmetically active substance, |
| 0.30-0.50% | by weight | of fragrance composition, |
| 0.05-0.15% | by weight | of at least one additive, |
| and up to 100% | by weight | of water |

in relation to the total weight of the cosmetic product.

12. The cosmetic product according claim 5, characterized in that it is in the form of an under-eye cream, and comprises:

| | | |
|---|---|---|
| 2.00-4.00% | by weight | of at least one humectant, |
| 0.50-1.00% | by weight | of at least one preservative, |
| 0.10-1.00% | by weight | of at least one thickening agent, |
| 4.50-6.50% | by weight | of at least one emulsifier, |
| 10.00-15.00% | by weight | of at least one emollient, |
| 0.50-1.50% | by weight | of the composition as defined in claim 1, |
| 5.00-10.00% | by weight, | of at least one additional cosmetically active substance, |
| 0.05-0.15% | by weight | of at least one additive, |
| and up to 100% | by weight | of water |

in relation to the total weight of the cosmetic product.

13. The cosmetic product according to claim 5, characterized in that it is in the form of a facial serum, and comprises:

| | | |
|---|---|---|
| 5.00-10.00% | by weight | of at least one humectant, |
| 0.50-1.00% | by weight | of at least one preservative, |
| 0.50-1.50% | by weight | of at least one thickening agent, |
| 3.00-5.00% | by weight | of at least one emulsifier, |
| 10.00-15.00% | by weight | of at least one emollient, |
| 0.50-1.50% | by weight | of the composition as defined in claim 1, |
| 0.10-1.00% | by weight | of at least one additional cosmetically active substance, |
| 0.20-0.40% | by weight | of fragrance composition, |
| 0.20-0.40% | by weight | of at least one additive, |
| and up to 100% | by weight | of water |

in relation to the total weight of the cosmetic product.

14. The cosmetic product according to claim 5, characterized in that it is in the form of a natural cream, and comprises:

| | | |
|---|---|---|
| 4.00-6.00% | by weight | of at least one humectant, |
| 0.60-1.30% | by weight | of at least one preservative, |
| 0.10-0.30% | by weight | of at least one thickening agent, |
| 3.50-4.50% | by weight | of at least one emulsifier, |
| 17.00-24.00% | by weight | of at least one emollient, |
| 0.50-1.50% | by weight | of the composition as defined in claim 1, |
| 0.15-0.50% | by weight | of at least one additive, |
| and up to 100% | by weight | of water |

in relation to the total weight of the cosmetic product.

15. The cosmetic product according to claim 5, characterized in that at least one additive is selected from the group consisting of at least one pH adjusting agent and at least one chelating agent and at least one colorant.

16. A method of manufacturing the composition according to claim 1 comprising the following steps:

a) preparing a mixture of composition hydroxyethylcellulose, components except lecithin and b) dissolving and hydrating lecithin in the resulting mixture, c) homogenizing the resulting mixture, and d) adding hydroxyethylcellulose and mixing the resulting composition.

17. The method according to claim 16, characterized in that the step of dissolving and hydrating lecithin is carried out for at least 24 hours.

18. A method of manufacturing the cosmetic product as defined in claim 5, characterized in that it comprises a) preparing an aqueous phase and heating it to an elevated temperature, b) preparing an oil phase and heating it to an elevated temperature, c) adding an emulsifier to the oil phase and mixing, d) adding the aqueous phase to the oil phase and homogenizing the resulting mixture, e) optionally cooling the resulting mixture and adding a UV filter, f) cooling the resulting mixture, g) adding cosmetically active ingredients, a preservative and optionally a fragrance composition, and then homogenizing the resulting mixture, h) further cooling the resulting mixture.

* * * * *